United States Patent
Haider et al.

(10) Patent No.: US 7,952,260 B2
(45) Date of Patent: *May 31, 2011

(54) ULTRASOUND IMAGING SYSTEM

(75) Inventors: Bruno Hans Haider, Ballston Lake, NY (US); Kjell Kristoffersen, Oslo (NO); Rayette Ann Fisher, Niskayuna, NY (US); Thomas Halvorsrod, Vestfold (NO); Robert Gideon Wodnicki, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/725,536

(22) Filed: Mar. 17, 2010

(65) Prior Publication Data

US 2010/0174195 A1    Jul. 8, 2010

Related U.S. Application Data

(63) Continuation of application No. 11/669,235, filed on Jan. 31, 2007, now Pat. No. 7,687,976.

(51) Int. Cl.
   *H01L 41/09*   (2006.01)
   *G01N 24/00*   (2006.01)
   *A61B 8/14*    (2006.01)

(52) U.S. Cl. .......... 310/334; 310/317; 310/319; 73/625; 600/459

(58) Field of Classification Search .................. 310/317, 310/319, 334; 73/625; 600/459
   See application file for complete search history.

(56) References Cited

U.S. PATENT DOCUMENTS

| | | | |
|---|---|---|---|
| 5,629,578 | A | 5/1997 | Winzer et al. |
| 6,013,032 | A | 1/2000 | Savord |
| 6,282,963 | B1 | 9/2001 | Haider |
| 6,346,079 | B1 | 2/2002 | Haider et al. |
| 6,491,634 | B1 | 12/2002 | Leavitt et al. |
| 6,506,160 | B1 | 1/2003 | Van Stralen et al. |
| 6,589,180 | B2 | 7/2003 | Erikson et al. |

(Continued)

FOREIGN PATENT DOCUMENTS

EP        1681019 B1    7/2006

(Continued)

OTHER PUBLICATIONS

Beyne, "The Rise of the 3rd Dimension for System Integration", Interconnect Technology Conference, 2006 International, pp. 1-5, Jun. 5-7, 2006.

(Continued)

Primary Examiner — Thomas M Dougherty
(74) Attorney, Agent, or Firm — Jason K. Klindworth

(57) ABSTRACT

An ultrasound imaging system (100). An exemplary system (100) includes a plurality of transducer elements (136) formed in subarrays (140) and a plurality of subarray circuit units (160'), with each circuit unit (160') connected to a subarray (140) of the transducer elements (136). The circuitry in each unit (160') comprises a plurality of integrated circuits (330, 340, 350), with at least a first (340) of the integrated circuits formed over a second (330) of the integrated circuits in a stacked configuration. In an example illustration the first integrated circuit (340) includes a first plurality of first bond pads (345) along a surface (342) thereof and the second integrated circuit (330) includes a second plurality of second bond pads (335) along a surface (331) thereof, with bond wires (344) extending between pairs of first and second bond pads to provide input/output signal connections therebetween.

12 Claims, 8 Drawing Sheets

U.S. PATENT DOCUMENTS

| | | | |
|---|---|---|---|
| 7,508,113 | B2 | 3/2009 | Daft et al. |
| 7,687,976 | B2 * | 3/2010 | Haider et al. ............. 310/334 |
| 2001/0043090 | A1 | 11/2001 | Savord |
| 2006/0118939 | A1 | 6/2006 | Fisher et al. |
| 2007/0016026 | A1 | 1/2007 | Thomenius et al. |
| 2008/0273424 | A1 | 11/2008 | Wodnicki et al. |

FOREIGN PATENT DOCUMENTS

| | | |
|---|---|---|
| WO | WO2006054260 A1 | 5/2006 |

OTHER PUBLICATIONS

Fisher et al., "Reconfigurable Arrays for Portable Ultrasound", 2005, IEEE Ultrasonics Symposium, vol. 1, pp. 495-499, Sep. 18-21, 2005.

Brunner, "Ultrasound System Considerations and Their Impact on Front-End Components", Analog Devices, Inc., 19 pages, 2002.

Co-pending U.S. Appl. No. 60/630,090, filed Nov. 22, 2004 entitled "Hybrid IC for Ultrasound Beamformer Probe".

* cited by examiner

ULTRASOUND IMAGING SYSTEM

CROSS-REFERENCES TO OTHER APPLICATIONS

This patent application is a Continuation of copending U.S. patent application Ser. No. 11/669,235, filed on Jan. 31, 2007.

BACKGROUND OF THE INVENTION

1. Field of the Invention

This invention relates to ultrasound imaging systems and, more particularly, to systems having beamforming electronics.

2. Background Art

Real time 3D ultrasound imaging for medical applications requires housing an array of perhaps several thousand transducer elements and associated signal processing electronics in a hand-held probe unit. In smaller systems (e.g., having only a few hundred array elements) it has been conventional to carry the transducer signals through a multi-wire cable to a system console containing essentially all of the processing circuitry for image generation. However, with larger arrays containing transducer elements numbering in the thousands, or in the tens of thousands or even more, it is difficult and impractical to perform all of the signal processing in a remote unit. This would require dedicated leads, each forming a separate connection between a transducer element and processing circuitry located in the console. To address this problem, a limited portion of the processing circuitry has been placed in the probe. For example, a large array of transducer elements may be divided into subarrays of uniform size, e.g., ranging from 10 to 40 transducer elements, with a dedicated unit of beam forming and processing circuitry for each subarray, herein referred as a subarray circuit unit. Each subarray circuit unit can combine the signals generated by all of the transducer elements in the subarray into a single channel or wire, e.g., by analog beam-formation. With this or other configurations, the signals received from all of the elements in the array can be transferred via a reduced number of cable leads to the processing circuitry in the console. In this way the thousands of signals can be transferred while retaining a manageable cable size.

To effect circuit functions in the probe, each subarray circuit unit normally includes high voltage transmitter circuitry, low voltage receiver circuitry and digital control circuitry. Implementation of these different circuit functions has required fabrication of multiple integrated circuits, e.g., Application Specific Integrated Circuits (ASICs), because the differing circuit functions have required different semiconductor manufacturing processes. The multiple ASIC components required for all of the subarray circuits have consumed a relatively large volume of available space in the probe unit. With the impracticality of fabricating all three functions in one monolithic die, the volume required for housing these subarray circuit units can be a factor limiting the practical size of a transducer array housed in a hand-held probe unit. Size and weight considerations influence the ease with which the hand-held probe unit can be maneuvered during examination procedures.

The need to reduce size and weight of probe units and consoles is especially relevant to portable ultrasound imaging systems which may be configured with note-book computer systems. Generally, size and weight are constraining factors which can limit achievable image quality of systems which use portable, hand-held probe units. Consequently, many hand-held probe units employ a relatively low number of transducer elements in order to minimize the amount of wiring and circuitry and thereby meet these criteria. Yet it is recognized that improved image quality can increase the diagnostic utility of these systems.

BRIEF DESCRIPTION OF THE INVENTION

In one embodiment an ultrasound imaging system includes an array of transducer elements formed in a matrix of subarrays, with each subarray containing a plurality of the transducer elements. Each subarray of transducer elements connected to a circuit unit, with circuitry in each unit including two or more integrated circuits in a stacked configuration, with each unit including transmission circuitry for generating acoustic signals, receiver circuitry for processing reflected signals and control circuitry. A system console is coupled to receive image information from the circuit units and includes image processing circuitry for displaying an image. All of the subarrays are positioned along a first plane, a first of the integrated circuits is positioned in a second plane parallel with the first plane and a second of the integrated circuits is positioned in a third plane parallel with the first plane.

In another embodiment, an ultrasound imaging system includes transducer elements formed in adjoining subarrays and subarray circuit units, each circuit unit being connected to a subarray of the transducer elements. Circuitry in each unit includes a plurality of integrated circuits, with at least a first of the integrated circuits formed over a second of the integrated circuits in a stacked configuration. A plurality of circuit board structures provide electrical connections between the transducer elements and the subarray circuit units. For at least one of the circuit units, the first integrated circuit includes a first plurality of first bond pads along a surface thereof and the second integrated circuit includes a second plurality of second bond pads along a surface thereof, and bond wires extend between pairs of first and second bond pads to provide input/output signal connections therebetween.

In still another embodiment, an ultrasound imaging system includes a transducer array probe unit and a system console for processing and displaying image data. The probe unit includes an array of transducer elements arranged in a matrix of subarrays, with each subarray containing a plurality of the transducer elements. A plurality of subarray circuit units each include multiple integrated circuits formed over one another in a stacked configuration. Each circuit unit is connected to one of the subarrays of transducer elements. A multi-wiring unit provides electrical connection between subarrays of transducer elements and subarrays of circuit units and provides input/output signal connections between at least the one subarray circuit unit and the system console. A plurality of removable clamps provide connections between one or more flexible circuits and the circuit board. A first of the integrated circuits is positioned in a first plane and a second of the integrated circuits is positioned in a second plane parallel with the first plane, with the first integrated circuit including a plurality of bond pads formed along a surface thereof, with the circuit unit including bond wires extending from some of the bond pads on the first integrated circuit to the second circuit to provide connections between the first and second integrated circuits.

BRIEF DESCRIPTION OF THE DRAWINGS

The invention will be more clearly understood when the following description is read in conjunction with the accompanying drawings, in which.

Like reference numbers are used throughout the figures to indicate like features. Individual features in the figures may not be drawn to scale.

DETAILED DESCRIPTION OF THE INVENTION

Figure 1:
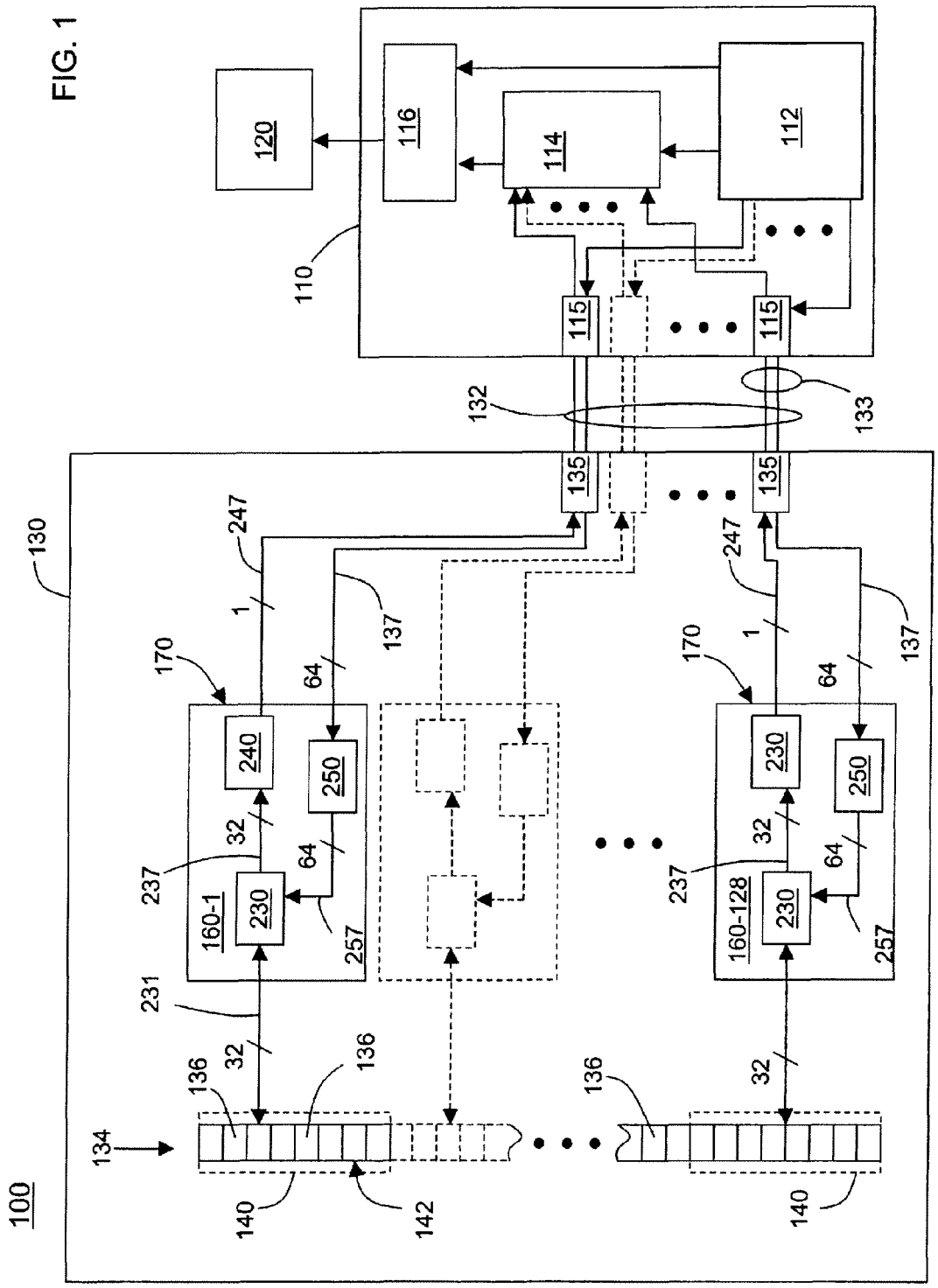
FIG. 1 is a simplified schematic diagram of an ultrasound imaging system.

FIG. 1 provides a partial view of an exemplary ultrasound imaging system 100 including a system console 110, a display 120 and a large area transducer array probe unit 130. The probe unit houses one hundred twenty eight subarray circuit units 160, sequentially referenced as 160-1 through 160-128. The probe unit 130 may be of the hand-held type. Information is transferred between the probe unit 130 and the system console 110 via a multi-wire cable 132 comprising one hundred twenty-eight signal lines 133. Each signal line 133 is coupled between a line connector 115 in the system console 110 and a line connector 135 in the probe unit 130. The console 110 receives image information from the subarray circuit units 160 through the signal lines 133 for processing by electronics including a system controller 112 coupled to primary beamforming circuitry 114 and a scan converter 116. The controller 112 is also coupled to the subarray circuit units 160 in the probe 130, providing overall control of the system 100. The primary beamforming circuitry 114 processes electrical signals received from individual subarray circuit units 160 to produce sector scan signals. The scan converter 116 having image processing circuitry converts the sector scan signals to raster signals suitable for image presentation on the display 120.

Figure 2:
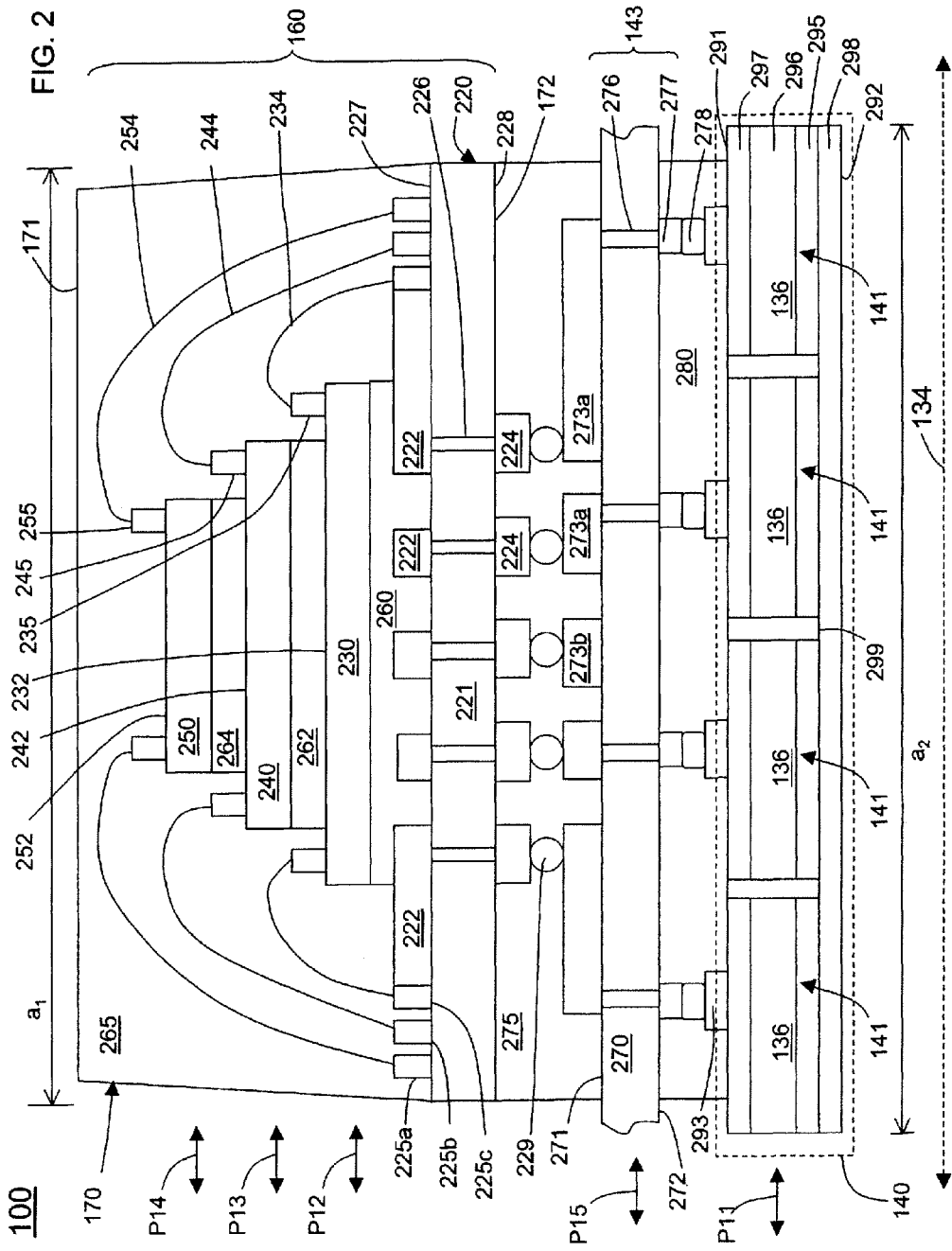
FIG. 2 provides a cross-sectional view of exemplary transducer and multi-chip module circuitry which may be formed in the system of FIG. 1.

Referring also to FIG. 2, the probe unit 130 includes a two-dimensional linear array 134 of transducer elements 136 connected to the subarray circuit units 160 through an interface formed with a multi-wiring unit 143. The exemplary transducer array 134 includes four thousand ninety-six transducer elements 136 arranged in a matrix of one hundred twenty-eight subarrays 140. Each subarray 140 has thirty-two transducer elements 136 arranged along four rows 141 and eight columns 142. Exemplary columns 142 of elements 136 are shown in FIG. 1 with phantom lines indicating groups of eight columns in a subarray 140. Four adjoining rows 141 of elements 136 are shown in FIG. 2, these corresponding to rows of one subarray 140. In this example, rows 141 and columns 142 are formed in orthogonal directions along a plane P11.

During operation each transducer element 136 in a subarray 140 transmits ultrasonic signals to and receives reflected ultrasonic signals from a subject, e.g., a patient undergoing examination. Each subarray circuit unit 160 comprises a transmitter ASIC 230, having circuitry for generating pulse signals and sending to the transducer element subarray 140; a receiver ASIC 240, having circuitry for processing of the reflected signals received from the transducer elements 136; and a controller ASIC 250 having transmit control circuitry for pulse timing. In each circuit unit 160, the controller ASIC 250 is formed over the receiver ASIC 240 which is formed over the transmitter ASIC 230, in a stacked configuration 170, also referred to herein as a multi-chip module 170. The specific order of stacking of the ASICs is variable and the example embodiment shown is one of multiple possible configurations. Also, the exemplary system partitioning of functionality between the ASICs 230, 240 and 250 is merely illustrative while there are numerous other possible groupings of transmitter, receiver, and control circuitry among various ASIC designs and various layers in the multi-chip module. The configuration of the multi-chip module 170 substantially reduces the size of the subarray circuit units 160 relative to systems having each of multiple integrated circuits positioned in the same plane for connection to a substrate, e.g., using a bail grid array.

In the multi-chip module 170 parasitic capacitance associated with electrical connections between ASIC devices within the unit 160 is significantly reduced because many of the bond wires effect relatively short distance connections which would otherwise be made with relatively long electrical traces formed in circuit boards.

As illustrated in FIG. 1, each controller ASIC 250 receives 64 signals from the system controller 112 along lines 137 and sends 64 transmit signals to the transmitter ASIC 230 along lines 257 in the multi-chip module 170. In response to a transmit signal, a transmitter ASIC 230 generates and sends 32 pulse signals to the transducer subarray 140. Each pulse signal travels along one of 32 individual lines 231 so that each transducer element 136 can receive a different pulse signal and, together, the elements in the array synthesize an acoustic signal of desired characteristics which propagates to an object under study. Elements in each subarray 140 then absorb energy of signals reflected from the subject, and the transmitter ASICs 230 receive electrical signals indicative thereof from the subarray 140 along one of the 32 individual lines 231. This signal information is transferred from the ASIC 230 to the receiver ASIC 240 along 32 individual lines 237 wherein information on the 32 lines is combined on to a single channel subarray signal line 247. In this manner, the number of signal lines in the cable 132 can be significantly reduced.

FIG. 2 illustrates connection of the ASICs 230, 240 and 250 in a subarray circuit unit 160 and connection to transducer element 136 in an associated subarray 140, having an upper surface 291 and a lower surface 292, via the multi-wiring unit 143. In this example, the multi-wiring unit 143 is a Flexible Circuit Board (FCB) 270 having a plurality of upper FCB traces 273, e.g., 273a, 273b, etc., formed along an upper surface 271 and a plurality of lower FCB contact pads 277 formed along a lower surface 272. A solder bump 278 is formed on each lower FCB contact pad 277. Adjacent transducer subarrays 140 of transducer elements 136 extend along the plane P11 defining, for purposes of orientation, horizontal directions such that a vertical orientation is normal to the plane P11 and upper and lower positions are relative to a horizontal direction.

In the multi-chip module 170, having an upper surface 171 and a lower surface 172, the controller ASIC 250 has a plurality of controller ASIC bond pads 255 along an upper surface 252 thereof, and the receiver ASIC 240 has a plurality of receiver ASIC bond pads 245 along an upper surface 242 thereof, and the transmitter ASIC 230 has a plurality of transmitter ASIC bond pads 235 along an upper surface 232 thereof. The ASIC 230 is formed on a routing substrate 220 having an upper surface 227, a lower surface 228, a plurality of substrate bond pads 225 (e.g., 225a, 225b and 225c) and a plurality of substrate vias 226. The substrate 220 comprises a layer 221 of insulative material, e.g., a polyimide resin film, laminated with conductive layers formed of copper or aluminum along the upper and lower surfaces 227 and 228, which are patterned and etched to form upper conductive traces 222 and lower conductive traces 224.

A plurality of controller ASIC bonding wires 254, receiver ASIC bond wires 244, and transmitter ASIC bond wires 234 provide electrical connections between the ASICs within each multi-chip module 170. In other embodiments, a heat spreader may be provided along the upper surface 171 of the multi-chip module 170 for enhancing heat removal from the package.

The controller ASIC bonding wires 254 electrically connect the controller ASIC bonding pads 255 to a first group 225a of the substrate bonding pads 225 on the routing substrate 220. The receiver ASIC bonding wires 244 electrically connect the receiver ASIC bonding pads 245 to a second group 225b of the substrate bonding pads 225 and the transmitter ASIC bonding wires 234 electrically connect the transmitter ASIC bonding pads 235 to a third group 225c of the substrate bonding pads 225. The substrate bonding pads 225 are connected to the patterned upper traces 222 for routing. Through vias 226, i.e., plated-through holes, in the routing substrate 220 electrically connect the upper traces 222 to the lower traces 224. Input/output (I/O) solder balls 229 formed on the lower traces 224 effect electrical connections between the multi-chip module 170 and the FCB 270 of the multi-wiring unit 143. The transmitter ASIC 230 is positioned in a second plane P12 parallel to and above the plane P11 for attachment to the upper surface 227 of the substrate 220 with a first adhesive layer 260. The receiver ASIC 240 is positioned in a third plane P13 parallel to and above the second plane P12 for attachment to the transmitter ASIC 230 with a second adhesive layer 262. The controller ASIC 250 is positioned in a fourth plane P14 above and parallel to the plane P13 for attachment to the receiver ASIC by a third adhesive layer 264. An insulative plastic mold cap 265 protectively encapsulates the ASICs 230, 240, and 250, the bond pads 235, 245, and 255, the bonding wires 234, 244, and 254, and the upper surface 227 of the substrate 220.

Individual transducer elements 136 each comprise a matching layer 295 formed against a piezoelectric material layer 296. The matching layer 295 provides suitable acoustic characteristics for transmitting acoustic energy to, and receiving acoustic signals from, the subject under study. The piezoelectric material layer 296 is formed over a lower or rear electrode 297 which is connected through a transducer contact pad 293 and a solder bump 278 to the multi-wiring unit 143. The rear electrode 297, the matching layer 295, and the piezoelectric material layer 296 in each transducer element are electrically isolated from like components of other transducer elements by a series of spaces or kerfs 299 which may be created by parallel sawing to create individual ones of the transducer components 296 and rear electrodes 297. A front electrode 298, typically formed of a relatively thin conductive material, is deposited over the matching layers 295 of elements 136 in the entire subarray 140 of transducer elements, providing a common ground for the subarray 140.

The transducer elements 136 may further include a dematching layer (not shown) or a backing layer having suitable acoustic characteristics to absorb or scatter acoustic energy transmitted in the direction away from an object under study. This prevents the acoustic energy from being reflected from structures or interfaces behind the transducer elements and back into the piezoelectric material. The acoustic backing material may consist of a composite of metal particles (e.g., tungsten) in an attenuating soft material such as rubber, epoxy or plastic. Other acoustic backing material compositions may also be used. The transducer elements may, for example, be lead zirconate titanate transducers (PZTs), capacitive Micromachined Ultrasonic Transducers (cMUTs), piezoelectric micromachined Ultrasonic Transducers (pMUTs), or PolyVinylidine DiFluoride (PVDF) transducers.

With each solder bump 278 formed on a lower FCB contact pad 277, a plurality of electrically conductive through-flex vias 276, extend from the upper surface 271 to the lower surface 272 of the FCB 270, and a first group 273a of the upper FCB traces 273 provide electrical connections between each transducer element 136 in the subarray 140 and the corresponding upper conductive trace 222. The upper trace 222 is connected to the transmitter ASIC 230 via the substrate bond pad 225c and the transmitter ASIC bond wire 234 connected to the transmitter ASIC bond pad 235. A second group 273b of the upper FCB traces 273 provides I/O connections (not shown) between the multi-chip module 170 and electronics in the system console. The multi-chip module 170 is attached to the upper surface 271 of the FCB 270 with a dielectric adhesive 275. The FCB 270, positioned along a fifth plane P15 parallel to the first plane P11, is attached along the upper surface 291 of each transducer subarray 140 with a dielectric adhesive 280. The FCB 270 may also serve as a dematching layer. In other embodiments, more than one flexible circuit board may form the multi-wiring unit 143 for I/O connections, and an additional dematching layer may be provided between the multi-chip module 170 and the FCB 270 or between the FCB 270 and the transducer subarrays 140.

Along the plane in which the view of FIG. 2 is taken, the lateral dimension $a_1$, as measured along the lower surface 172 of the multi-chip module 170, is less than or equal to the lateral dimension $a_2$, measured along the lower surface 292 of the transducer subarray 140. This enables formation of a large matrix of subarrays 140 without having a substantial gap between adjacent subarrays 140.

Figure 3:
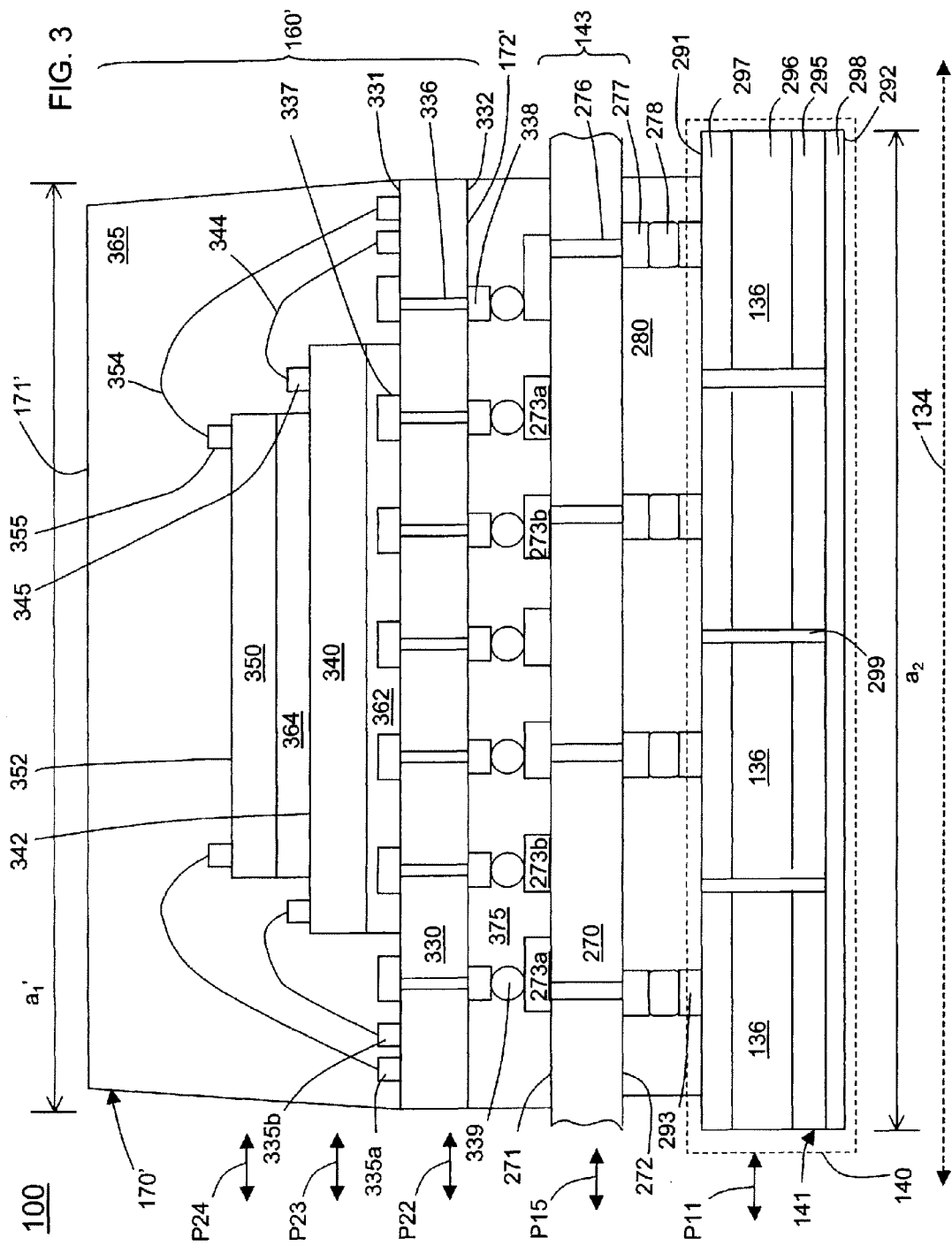
FIG. 3 provides a cross-sectional view of another example of transducer and multi-chip module circuitry which may be formed in the system of FIG. 1.

FIG. 3 illustrates a second multi-chip module 170' wherein a plurality of subarray circuit units 160', in lieu of the circuit units 160, are each connected to the transducer element subarray 140 via the multi-wiring unit 143 as described with respect to FIG. 2 with adjacent transducer subarrays 140 of transducer elements 136 extending along the plane P11.

Each multi-chip module 170', having upper and lower surfaces 171', 172', includes a series of ASICs in a stacked configuration. A controller ASIC 350, having a plurality of bond pads 355 formed along an upper surface 352 thereof, is formed over a receiver ASIC 340, having a plurality of bond pads 345 formed along an upper surface 342 thereof; which is formed over a transmitter ASIC 330 having a plurality of bond pads 335 formed along an upper surface 331 thereof. The transmitter ASIC 330 further includes a plurality of through-die vias 336, and a plurality of contact pads 338 formed along a lower surface 332. In this example, the ASIC 330, the lower-most of the three ASIC die in the multi-chip module 170', serves as a routing substrate for circuitry on the controller ASIC 350 and the receiver ASIC 340. A plurality of controller ASIC bonding wires 354 and a plurality of receiver ASIC bonding wires 344 extend from the ASIC 330 to provide electrical connections among the three ASICs in the multi-chip module 170'.

The controller ASIC bonding wires 354 electrically connect the controller ASIC bonding pads 355 to a first group 335a of transmitter ASIC bonding pads 335. The receiver ASIC bonding wires 344 electrically connect the receiver ASIC bonding pads 345 to a second group 335b of the transmitter ASIC bonding pads 335. Routing among ASICs is provided via a metallization structure (not shown) within the transmitter ASIC die 330. The transmitter ASIC bonding pads 335 are connected to the through-die vias 336, which may be filled with conductive material such as copper or aluminum, via upper traces 337 formed along the upper surface 331. The through-die vias 336 electrically connect the bond pads 335 to the contact pads 338 formed along the lower surface 172'. Input/output (I/O) solder balls 339 are formed on the contact pads 338 for I/O connections. Accordingly, the ASICs 330, 340, and 350 are electrically connected to the solder balls 339. The transmitter ASIC 330 having wiring patterns or traces 337 is positioned in a second plane P22 parallel to the plane P11 and attached to the upper surface of the FCB 270 with a dielectric adhesive layer 375. The receiver ASIC 340 is positioned along a third plane P23 parallel to the second plane P22 and is attached to, and vertically spaced from, the transmitter ASIC 330 with an adhesive layer 362. The controller ASIC 350 is positioned along a fourth plane P24 also parallel to the second plane P22 and is attached to the receiver ASIC 340 with another adhesive layer 364. An insulative plastic mold cap 365 protectively encapsulates the ASICs 340 and 350, the bonding wires 344 and 354, the bond pads 335, 345 and 355, and the upper surface 331 of the transmitter ASIC 330.

In the plane along which the view of FIG. 3 is taken, the lateral dimension $a_1$ of the multi-chip module 170', taken along the lower surface 172', is less than or equal to the lateral dimension $a_2$ of the transducer subarray 140, taken along the lower surface 292'. This enables formation of a large matrix of subarrays 140 without a substantial gap between the adjacent subarrays 140.

Figure 4:
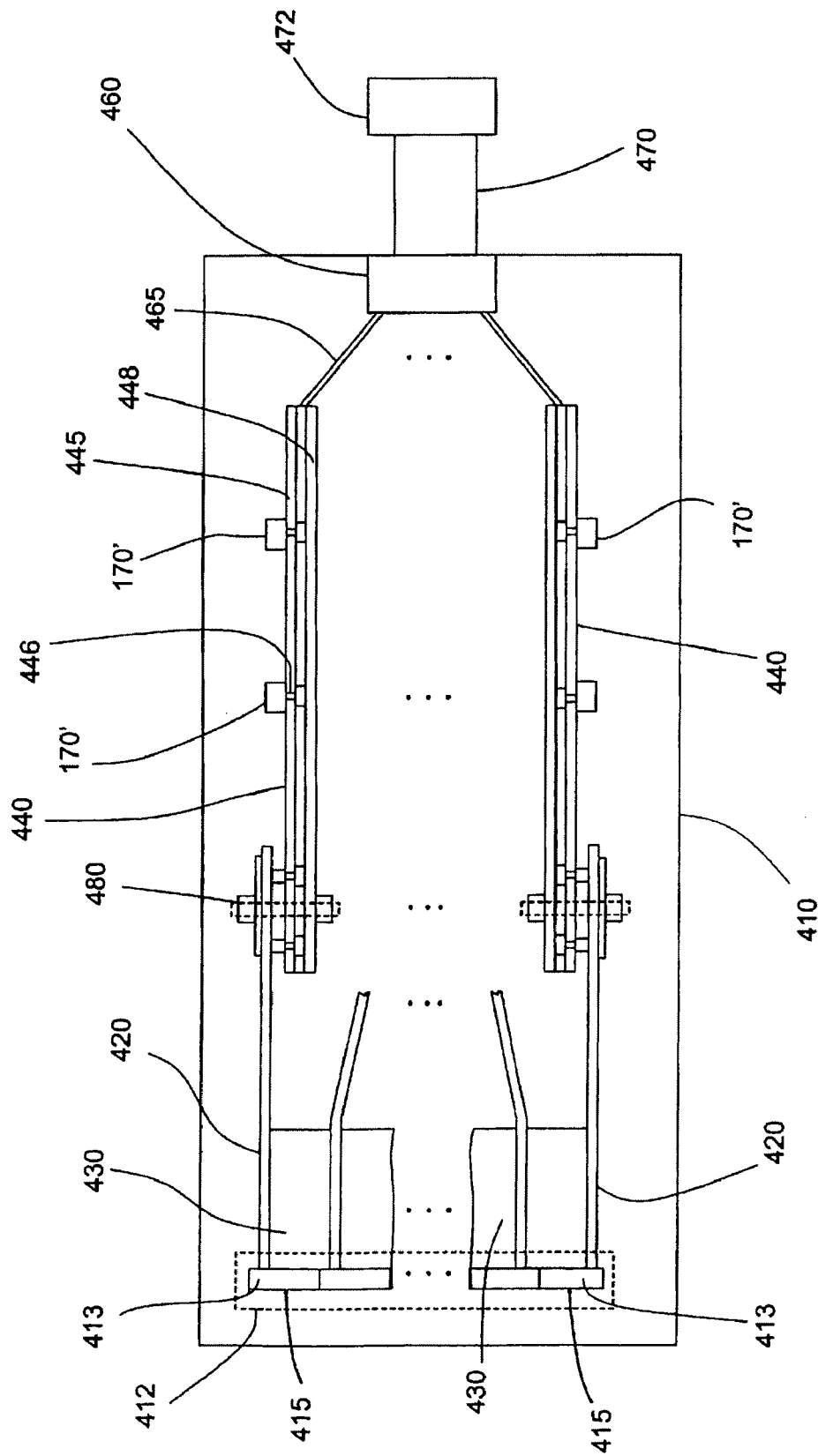
FIG. 4 is a cross-sectional view of an exemplary probe unit suitable for incorporation in the system of FIG. 1.

According to another embodiment, FIG. 4 illustrates in a partial cross-sectional view a probe unit 410 for the system 100 comprising a plurality of the multi-chip modules 170' as described with reference to FIG. 3. The probe 410 comprises a two-dimensional array 412 of transducer elements 413, a plurality of flexible circuits 420 or flexes having electrical traces (not shown), and a plurality of Printed Circuit Boards (PCBs) 440 each having one or more multi-chip modules 170'. The transducer elements 413 are arranged in a plurality of subarrays 415, each subarray 415 comprising one row of transducer elements 413. Each subarray 415 is coupled to a flex circuit 420 for connection to a corresponding multi-chip module 170'. The flexes 420 are separated from each other by a non-conducting spacer 430 formed of material such as epoxy. Each flex 420 is joined to a corresponding PCB 440 by one or more removable clamps 480. A plurality of flexible connectors 465 connects the PCBs 440 with a probe line connector 460. A cable bundle 470 couples the probe line connector 460 to a system line 472 in order to transfer signals between the multi-chip modules 170' and an electronic components such as the main beamformer 114 illustrated in FIG. 1.

Connection of the flexes 420 to the PCB's 440 by clamps 480 allows for separate fabrication and assembly of components. Thus, the transducer array 412 may be conventionally fabricated under low temperature conditions and assembled with the flexes 420 in a process which is separate and isolated from the relatively high temperature assembly of components which form the PCB's 440. The multi-chip modules 170' can be mounted onto the PCBs 440 at a temperature greater than 250 C in a reflow oven without exposing the transducers 415 to high temperature conditions. Also, with separate and isolated processes, the transducer array 412 can undergo physical processing, such as sawing and grinding operations, without exposing sensitive components in the PCB 440 to contaminants. Otherwise, electrically conductive particles generated during grinding operations could cause shorts in the PCB components. The clamp connection effects assembly of flexes 420 and PCBs 440 after the transducer array 412 is fabricated in isolation from steps relating to fabrication and assembly of the PCB components. Thus fabrication steps for each component can be optimized without concern that another component may be degraded. Each flex 420 can be coupled to a corresponding PCB with mating connectors, an anisotropically conductive film, bump bonding or hot bar bonding. When clamp connections or the mating connectors are employed, the flex 420 and the PCB 440 can be readily and repeatedly coupled and decoupled. This facilitates repair of the probe unit 410 when failures occur in either the transducer array 412 or the PCB 440, allowing for replacement of defective components without discarding the other components.

Figure 5:
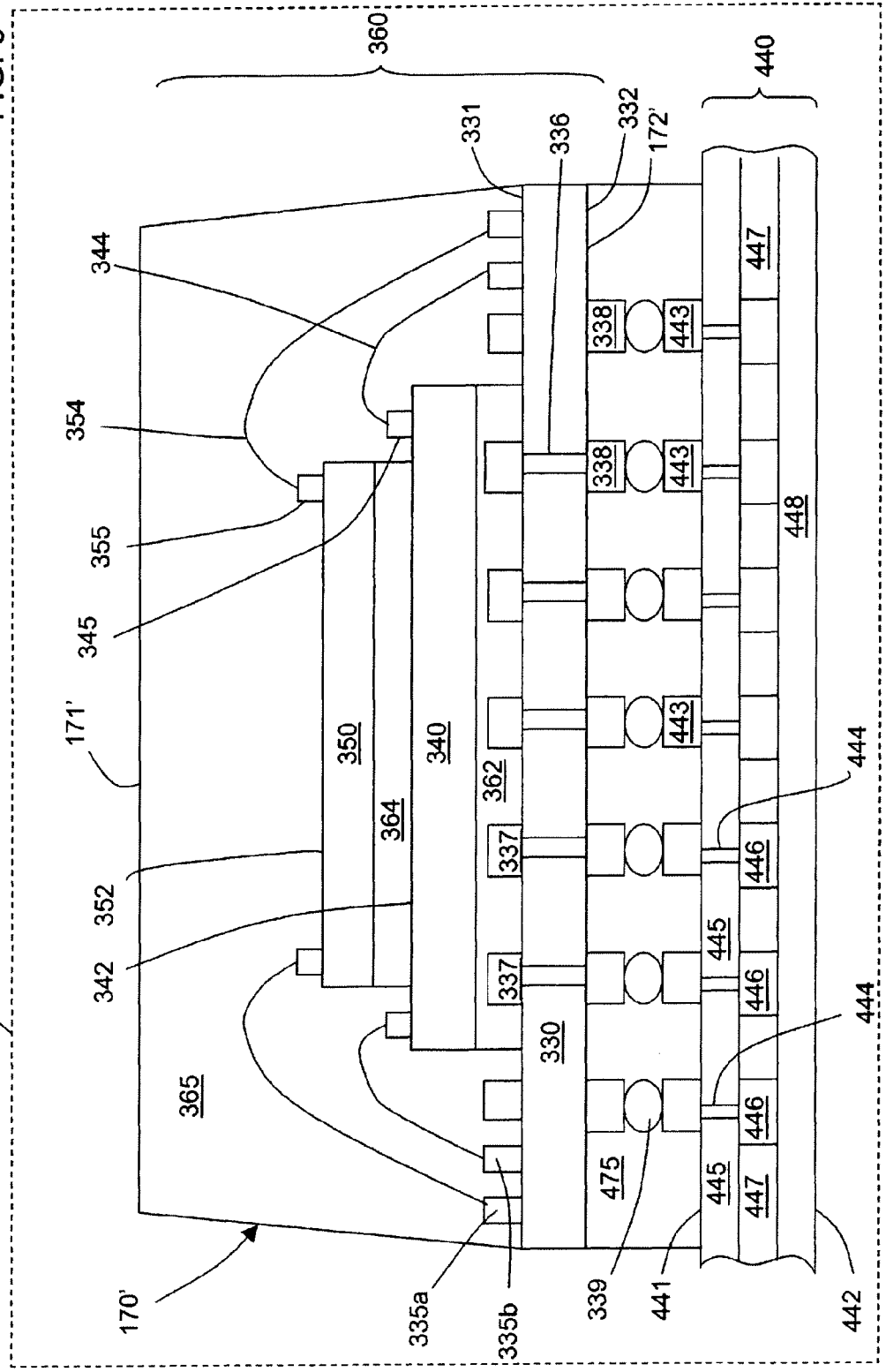
FIG. 5 is a cross-sectional view illustrating a multi-chip module in the probe unit of FIG. 4.

FIG. 5 illustrates for the system 100 exemplary electrical connections between the multi-chip module 170' (illustrated in FIG. 3) and one of the PCBs 440 shown in FIG. 4. With each multi-chip module 170' including controller ASIC 350 positioned over a receiver ASIC 340 positioned over a transmitter ASIC 330, a plurality of contact pads 338 are formed along the lower surface 332 of the transmitter ASIC. Input/output (I/O) solder balls 339 are formed on the contact pads 338 for I/O connections. The transmitter ASIC bonding pads 335 are connected to the through-die vias 336 by the upper traces 337. The PCB 440 having an upper surface 441 and a lower surface 442, comprises three adjoining dielectric layers 445, 447 and 448. PCB contact pads 443 are formed along the upper surface 441 providing connection between I/O solder balls 339 and upper level vias 444, formed in the upper level dielectric layer 445. The vias 444 contact underlying inner conductors 446 formed in the intra-level dielectric 447. The transmitter ASIC 330 is attached to the upper surface 441 of the PCB 440 with a dielectric adhesive layer 475. The PCB 440 provides electrical connection between the transducer subarrays 415 and the multi-chip modules 170' and also provides electrical connection between the multi-chip modules 170' and electronics in the system console 110 shown in FIG. 1.

Figure 6:
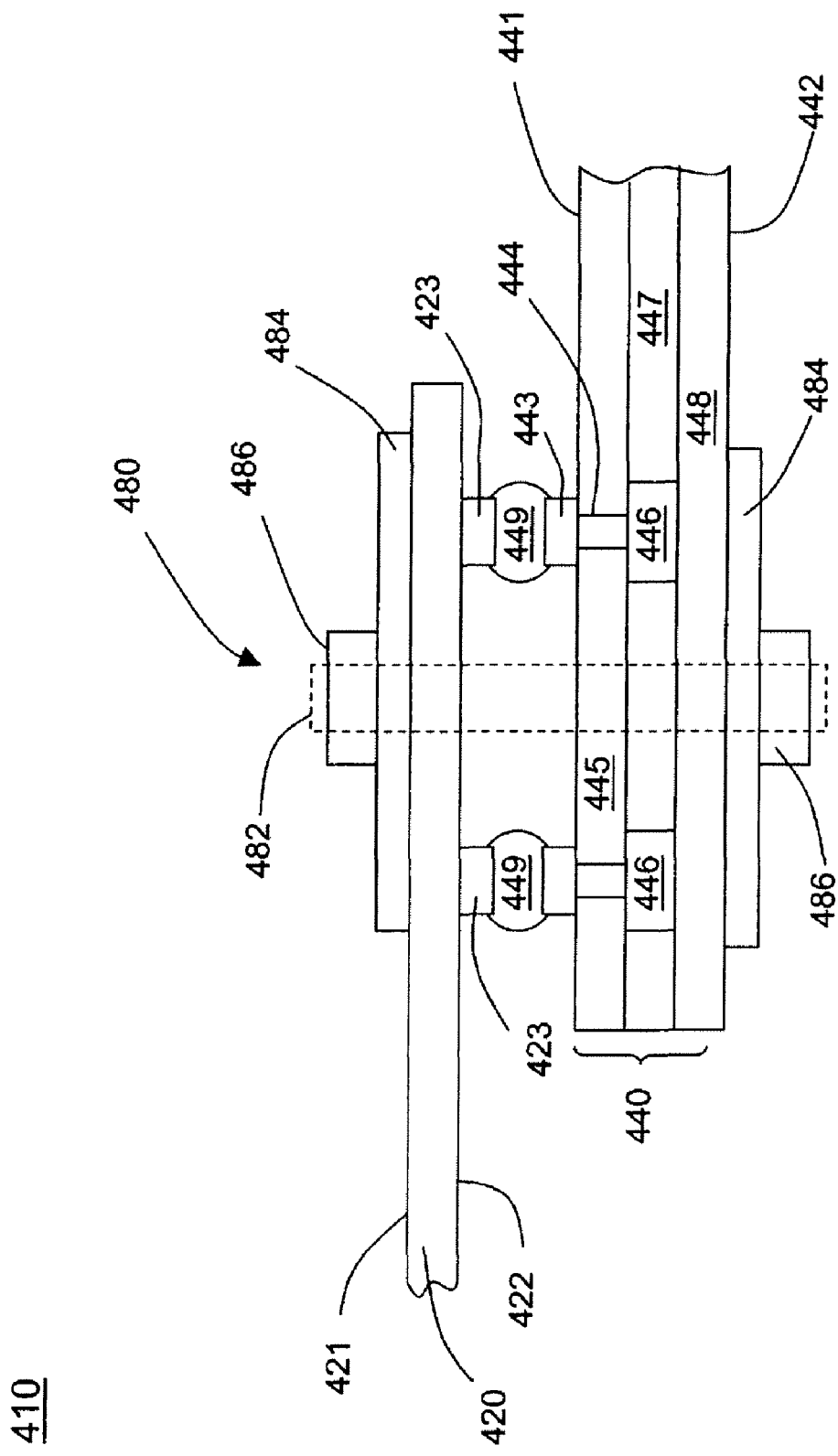
FIG. 6 is a cross-sectional view further illustrating features of the probe unit shown in FIG. 4.

An exemplary electrical connection between a PCB 440 and a flex 420 with one or more clamps 480 is illustrated in the partial cross-sectional view of FIG. 6. As described with respect to FIG. 6, the PCB 440 includes an upper surface 441, a lower surface 442, and three adjoining dielectric layers: upper layer 445, intra-level layer 447 and lower layer 448. One or more contact pads 443 are formed along the upper surface 441, and upper level vias 444 are formed in the upper level dielectric layer 445. Underlying inner conductors 446 are formed in the intra-level dielectric 447. A plurality of gold bumps 449 are formed on the PCB contact pads 443. The flex 420, having an upper surface 421 and a lower surface 422 includes flex contact pads 423 formed along the lower surface 422. For simplicity of illustration, only two PCB contact pads 443 and two flex contact pads 423 are shown in FIG. 6. One or more holes are provided in the flex 420 and in the PCB 440 for clamping. Each clamp 480 comprises a connecting bolt 482, a pair of washers 484 and a pair of nuts 486. After clamping holes of the flex 420 are aligned with clamping holes of the PCB 440, the clamp bolts 482 are inserted and secured with washers 484 and nuts 486. The clamping pressure effects electrical contacts between the gold bumps 449, the flex contact pads 423 and the PCB contact pads 443. Alternately, the flex contact pads 423 and the PCB contact pads 443 may be bonded together by compression. The bonding may be effected by gold plating of the contact pads 423 and 443 prior to compression.

Figure 7:
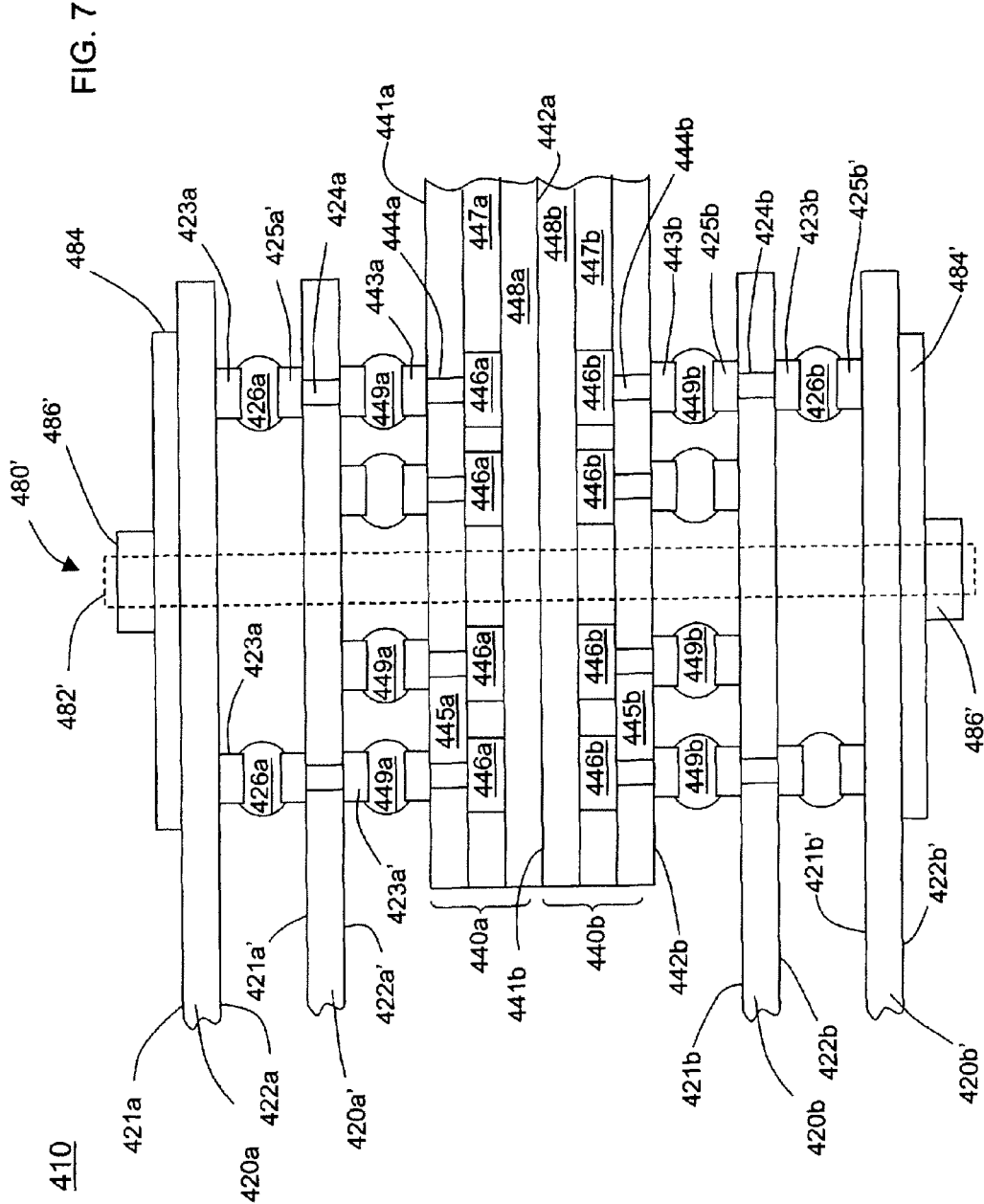
FIG. 7 is a cross-sectional view further illustrating features of the probe unit shown in FIG. 4.

In an embodiment shown in the partial cross-sectional view of FIG. 7, electrical connection between the flexes 420 and the PCBs 440 is also effected by clamping. Two PCBs 440a and 440b and four flexes 420a, 420a', 420b and 420b' are joined by one or more clamps 480'. The first PCB 440a is coupled to the first and second flexes 420a and 420a' and the second PCB 440b is coupled to the third and fourth flexes 420b and 420b'. In other embodiments, more than two flexes 420 may be coupled to a PCB 440.

The first flex 420a having an upper surface 421a and a lower surface 422a, has two flex contact pads 423a formed along the lower surface 422a, herein referred as first flex lower contact pads 423a. The second flex 420a' having an upper surface 421a' and a lower surface 422a', has two flex contact pads 425a' formed along the upper surface 421a', herein referred as second flex upper contact pads 425a'. Four flex contact pads 423a' are formed along the lower surface 422a'. The second flex 420a' further includes two through-flex vias 424a which provide connection between the second flex upper contact pads 425a' and the second flex lower contact pads 423a'. Each of the lower contact pads 423a of the first flex 420a is coupled to a corresponding flex trace (not shown) of the first flex 420a and each of the lower contact pads 423a' of the second flex 420a' is coupled to a corresponding flex trace (not shown) of the second flex 420a'. The third flex 420b having an upper surface 421b and a lower surface 422b, has four upper flex contact pads 425b formed along the upper surface 421b, and two lower flex contact pads 423b formed along the lower surface 422b. The third flex 420b further includes two through-flex vias 424b which provide connection between the third flex upper contact pads 425b and the third flex lower contact pads 423b. The fourth flex 420b' having an upper surface 421b' and a lower surface 422b', has two upper flex contact pads 425b' formed along the upper surface 421b'. Each upper contact pad 425b of the third flex 420b is coupled to a corresponding flex trace (not shown) of the third flex 420b and each upper contact pad 425b' of the fourth flex 420b' is coupled to a corresponding flex trace (not shown) of the fourth flex 420b'. One or more holes (not shown) are provided in the flexes 420 for clamping.

The first PCB 440a having an upper surface 441a and a lower surface 442a, includes PCB first contact pads 443a formed along the upper surface 441a, upper level vias 444a formed in an upper level dielectric layer 445a, underlying inner conductors 446a formed in an intra-level dielectric 447a, and a layer of dielectric 448a. The second PCB 440b, having an upper surface 441b and a lower surface 442b, includes second PCB contact pads 443b formed along the lower surface 442b, lower level vias 444b formed in a lower level dielectric layer 445b, underlying inner conductors 446b formed in an intra-level dielectric 447b, and an overlying layer of dielectric 448b. One or more holes (not shown) are provided in the PCBs 440 for clamping. Each clamp 480' comprises a connecting bolt 482', a pair of washers 484' and a pair of nuts 486'. A plurality of gold bumps 426 (e.g., 426a, 426b) are formed on the second flex upper contact pads 425a' and the fourth flex upper contact pads 425b'. A plurality of gold bumps 449 (e.g., 449a, 449b) are formed on the first PCB contact pads 443a and on the second PCB contact pads 443b. After the clamping holes of the flexes 420 and the PCBs 440 are aligned, the clamp bolts 482' are inserted and secured with washers 484' and nuts 486'. The clamping pressure effects electrical contacts between gold bumps 426, 449 and flex contact pads 423. In other embodiments, the flexes 420 may be attached to semi-rigid Flexible Circuit Boards (FCBs) having one or more multi-chip modules. In still other embodiments, the multi-chip modules 440 may be mounted directly onto the flex circuits 420.

Figure 8:
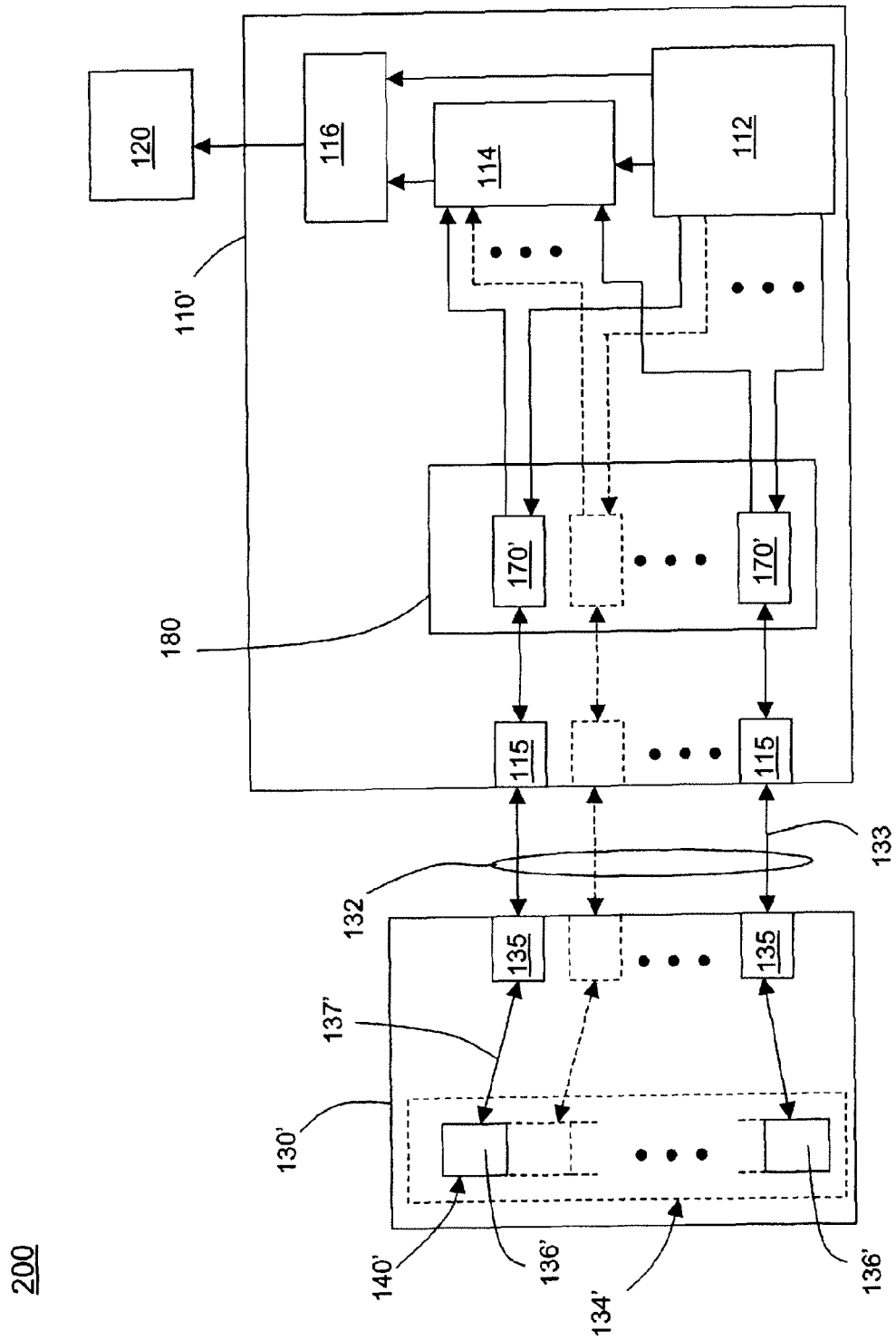
FIG. 8 illustrates an ultrasound imaging system according to an embodiment of the invention.

FIG. 8 illustrates another embodiment comprising multi-chip modules 170' in an ultrasound imaging system 200. The exemplary ultrasound imaging system 200 includes a system console 110', a display 120 and a transducer array probe 130'. In FIG. 8 the multi-chip modules 170' are placed in the system console 110'. The probe 130' comprises an array 134' of transducer elements 136'. The transducer elements 136' are arranged in a plurality of subarrays 140', each subarray 140' comprising one row of transducer elements 136'. Information is transferred between the probe 130' and the system console 110' via a multi-wire cable 132. Each wire 133 in the cable 132 is coupled to the system console 110' and to the probe 130' by a system line connector 115 and a probe line connector 135, respectively. A flexible circuit 137' connects a subarray 140' of transducer elements 136' to a corresponding probe line connector 135. The console 110' includes a system controller 112 coupled to primary beamforming circuitry 114, a scan converter 116, and a plurality of multi-chip modules 170' having transmission circuitry, receiver circuitry, and controller circuitry. The multi-chip modules 170' are mounted on a PCB 180. The system controller 112 may directly provide timing signals to transmission circuitry in the multi-chip module 170' which eliminates the need for controller circuitry in the multi-chip module 170'. The primary beamformer 114 receives electrical signals from individual multi-chip modules 170' and processes the signals to produce sector scan signals. The scan converter 116 converts the sector scan signals to raster display signals suitable for presentation on the display 120.

Embodiments of multi-chip modules 170 in an ultrasound imaging system have been described. The multi-chip modules 170 may be directly coupled to a subarray 140 of transducers 142. The modules 170 may be coupled via flexible circuits 420 and PCBs 440 in a probe 410 as illustrated in FIG. 4. The modules 170 may be mounted on a PCB in a system console 110 as shown in FIG. 8. Each multi-chip module can comprise a series of stacked integrated circuit die, e.g., formed by stacking a controller ASIC, a receiver ASIC, and a transmitter ASIC. The multi-chip module may also comprise beamformer circuitry. Multi-chip module configurations provide a significant reduction in volumetric space requirements of a subarray circuit unit 160. This enables tiling of relatively dense subarrays 140 to form a high density relatively large area transducer array in a hand-held probe. The multi-chip module configuration provides a reduction in size and an improvement in performance, e.g., reduced parasitic capacitance.

While several embodiments of the invention have been illustrated and described, the invention is not so limited. Numerous modifications, variations, substitutions and equivalents will occur to those skilled in the art without departing from the spirit and scope of the present invention as described in the claims.

The invention claimed is:

1. An ultrasound imaging system of the type which generates an image of an object under observation, comprising:
 a plurality of transducer elements arranged along a plane;
 a plurality of circuit units, each separately coupled to at least one of the plurality of transducer elements, circuitry in at least one circuit unit comprising two or more integrated circuits in a stacked configuration, with at least one circuit unit comprising transmission circuitry for generating the acoustic signals, receiver circuitry for processing of the reflected signals and control circuitry; and a system console coupled to receive image information from the circuit units and comprising image processing circuitry for displaying an image of the object, wherein all of the transducer elements are positioned along a first plane, a first of the integrated circuits is positioned in a second plane parallel with the first plane and a second of the integrated circuits is positioned in a third plane parallel with the first plane.

2. The system of claim 1 further comprising a multi-wiring unit providing electrical connection between the transducer elements and the circuit units, and providing input/output signal connections between the circuit units and a multi-wire cable for connection to the system console.

3. The system of claim 2 wherein the multi-wiring unit comprises one or more flexible circuit boards having a plurality of electrically conductive through-flex vias.

4. The system of claim 2 wherein the multi-wiring unit is positioned in a fourth plane parallel with the first plane.

5. The system of claim 1 wherein at least one of the circuit units is formed on a routing substrate for conducting electrical signals between the integrated circuits in the circuit unit and providing input/output signal connections to the circuit unit.

6. The system of claim 5 wherein the routing substrate comprises conductive through vias for providing signals between each circuit unit and individual ones of the plurality of transducer elements.

7. The system of claim 1 wherein all of the circuit units are positioned in a hand-held probe unit.

8. The system of claim 1 wherein the first integrated circuit in each circuit unit comprises wiring patterns and bond wires for conducting electrical signals between the first and second integrated circuits in the circuit unit and providing input/output signal connections for the circuit unit.

9. The system of claim 8 comprising a third integrated circuit and additional bond wires extending from bond pads on the first integrated circuit to effect connections between the second and third integrated circuits.

10. The system of claim 1 wherein the second plane is positioned between the first and third planes and the first integrated circuit, and comprises conductive through vias for providing signals between each circuit unit and individual ones of the plurality of transducer elements.

11. The system of claim 1 wherein the transducer elements are each selected from the group consisting of a lead zirconate titanate transducer (PZT), a capacitive Micromachined Ultrasonic Transducer (cMUT), a piezoelectric Micromachined Ultrasonic Transducer (pMUT), and a PolyVinylidine DiFluoride (PVDF) transducer.

12. The system of claim 1 wherein the transducer elements arranged along a plane are arranged in a matrix of subarrays, with each subarray containing a plurality of the transducer elements, for generating acoustic signals and receiving reflections of the signals.

* * * * *